(12) United States Patent
Michel

(10) Patent No.: US 7,510,603 B2
(45) Date of Patent: Mar. 31, 2009

(54) TATTOOING INK

(76) Inventor: Ralf Michel, Wachthausgasse 1, Landau (DE) 76829

( * ) Notice: Subject to any disclaimer, the term of this patent is extended or adjusted under 35 U.S.C. 154(b) by 0 days.

(21) Appl. No.: 11/574,436

(22) PCT Filed: Sep. 6, 2005

(86) PCT No.: PCT/EP2005/009537

§ 371 (c)(1), (2), (4) Date: Sep. 10, 2008

(87) PCT Pub. No.: WO2006/027200

PCT Pub. Date: Mar. 16, 2006

(65) Prior Publication Data

US 2009/0000513 A1    Jan. 1, 2009

(30) Foreign Application Priority Data

Sep. 6, 2005    (DE) .................. 20 2004 014 053 U

(51) Int. Cl.
*C09D 11/00*    (2006.01)

(52) U.S. Cl. .................................... 106/31.03; 424/422
(58) Field of Classification Search .............. 106/31.03; 424/422

See application file for complete search history.

(56) References Cited

U.S. PATENT DOCUMENTS

| | | | |
|---|---|---|---|
| 6,013,122 A | 1/2000 | Klitsman et al. | |
| 6,192,890 B1 * | 2/2001 | Levy et al. | 128/899 |
| 6,800,122 B2 * | 10/2004 | Anderson et al. | 106/31.03 |
| 6,881,249 B2 * | 4/2005 | Anderson et al. | 106/31.03 |
| 2002/0100425 A1 * | 8/2002 | Meyers et al. | 119/174 |
| 2005/0172852 A1 * | 8/2005 | Anderson et al. | 106/31.03 |

FOREIGN PATENT DOCUMENTS

WO    99/07777 A    2/1999

* cited by examiner

*Primary Examiner*—Helene Klemanski
(74) *Attorney, Agent, or Firm*—David A. Guerra

(57) ABSTRACT

The invention relates to a tattooing ink containing water, colored pigments, and a binding agent for binding the colored pigments with the water. Said tattooing ink also contains another constituent in the form of bioactive glass.

20 Claims, No Drawings

TATTOOING INK

CROSS-REFERENCE TO RELATED APPLICATIONS

This application is an U.S. national phase application under 35 U.S.C. §371 based upon co-pending International Application No. PCT/EP2005/009537 filed on Sep. 6, 2005. Additionally, this U.S. national phase application claims the benefit of priority of co-pending International Application No. PCT/EP2005/009537 filed on Sep. 6, 2005 and German Application No. 20 2004 014 053.5 filed on Sep. 7, 2004. The entire disclosures of the prior applications are incorporated herein by reference. The international application was published on Mar. 13, 2006 under Publication No. WO 2006/027200 A1.

BACKGROUND OF THE INVENTION

1. Field of the Invention

The invention relates to a tattooing ink containing water, colored pigments and a binding agent for binding the colored pigments with the water.

2. Description of the Prior Art

Originally, for tattooing purposes an incision was made into the skin in an archaic manner, the wound subsequently being dyed with ink, ash or other coloring substances. Nowadays, the dye is introduced into the skin by a needle in order to make a picture or text permanently visible on the skin. The dye is introduced into the skin at the same time the skin is being pierced. The prick must neither be too superficial, nor must it penetrate too deeply. If the dye is introduced merely into the outermost skin layer, i.e. into the cell layers of the epidermis, the dye particles are washed out and shed in the course of constant renewal of the epidermis. If the dye is introduced into the skin too deeply, bleeding will occur, which results in a wash-out of the dye from the skin.

However, any type of tattooing injures the skin, if a dye is injected into or under the skin, respectively. This may cause inflammation. It is, therefore, not only important to pay attention to special cleanliness and to use sterilized instruments, but also to use dyes having specific properties, which reduce the risk of inflammation.

Up until about the end of the $20^{th}$ century for the most part dyes were used consisting of water, alcohol, glycerin, rose water, in part, and colored pigments. Modern dyes are normally free of alcohols. They are based on an aqueous solution containing pigments as dye particles.

Apart from specific tattooing dyes, ink is nowadays also still used for tattooing purposes, like it was practiced even decades ago. The ink consists likewise of colored pigments and water. In order to overcome the hydrophobic properties of the pigments, additional binding agents are used for all modern dyes. This counteracts the material separation of water and pigment, so that the pigment is dispersed in the water.

Shellac is often used as a binding agent, partially in combination with other substances. Ink as well normally contains shellac as a binding agent. In the case of tattooing inks, shellac is always combined with other substances. To black tattooing ink mainly a mixture of shellac and borax is added. This is a reasonably priced mixture, which is adequate for common dyes. High-quality tattooing inks and colored dyes on the other hand are often based on a combination of shellac and ammonia. In addition, so-called povidones are also known as binding agents, which serve as binding agents to regulate viscosity.

Modern tattooing inks of qualified manufacturers have in common that they possess good color and/or light fastness. They are also not hazardous to health to the extent that they have been tested for heavy metal contaminants and do not contain carcinogenic aromatic amines.

SUMMARY OF THE INVENTION

It is the object to provide high-quality tattooing ink with good light fastness, which can be readily processed and which is anti-microbial, anti-inflammatory and optimized with regard to tolerability.

DESCRIPTION OF THE PREFERRED EMBODIMENT

The tattooing ink according to the invention is composed of water, colored pigments, a binding agent and bioactive glass as a further constituent. The water contained in the tattooing ink is normally demineralized or distilled water. The pigments include various colors so that almost any hues from white to black can be produced.

The bioactive glass is present in the tattooing ink in relatively small proportions. The glass is mainly based on a mixture containing predominantly silicon dioxide. Other constituents may be oxides of the alkali metals and the alkaline earth metals. Moreover, additional constituents may be present in the glass mixture. The bioactive glass has the effect of being anti-inflammatory. This prevents the occurrence and possible spreading of inflammations which may occur during penetration of the tattooing needle into the skin. Moreover, wound healing is promoted. The healing process of the skin lacerated by the tattooing needle is accelerated by the glass contained in the dye. Skin irritations are likewise reduced and eased very rapidly due to the added glass particles.

Apart from these positive effects of the glass particles as constituents of the tattooing ink according to the invention, the color properties such as light fastness and color fastness are not impaired by the glass. The glass itself is very well tolerated, since it is a material to which even sensitive skin does not react by irritations. In other respects as well, the glass does not cause skin reactions or even inflammations. As a whole, a tattooing ink is thus provided, which, apart from the pigments, is free of sensitizing ingredients.

The glass particles contained in the tattooing ink further exhibit an anti-microbial action. The formation of germs in the tattooing ink is thus reliably prevented. This is of particular importance if tattooing ink is removed from an ink bottle more than once. In addition, the efficacy against certain mold fungi and yeasts has been scientifically proven; since it may happen that after opening the bottle and after the first withdrawal of tattooing ink bacteria may enter into the ink. Due to the anti-microbial action of the glass, the bacteria are, however, destroyed. Even if ink is removed from an ink bottle more than once, no health risks occur. Storage of opened ink bottles is likewise no longer a problem.

In a preferred embodiment of the tattooing ink, the binding agent for binding the colored pigments with the water is a povidone. In this case, in particular, polyvinyl-pyrrolidone is used. This binding agent provides very good binding of the colored pigments with the water. The povidone creates structures in the water, which keep the colored pigments suspended, as it were.

A tattooing ink, whose constituents are present in the following composition is particularly advantageous: the ink has a water content of 35 wt. % to 65 wt. %. The pigments represent a proportion of 1 wt. % to 40 wt. %. A povidone is represented in a proportion of 5 wt. % to 20 wt. %; crospovidones are present in a proportion of 0.1 wt. % to 2.5 wt. %. The tattooing ink contains glass particles in a proportion of 0.1 wt. % to 10 wt. %.

The composition of the tattooing ink varies as a function of the color composition. Thus, black tattooing ink has a colored pigment content of 8 wt. % to 16 wt. %. A white tattooing ink has a pigment content between 35 wt. % and 40 wt. %. The content of the povidones used is mainly in the region of between 7.5 wt. % and 17.5 wt. %, a povidone content of 17.5 wt. % being preferred. Likewise, a tattooing ink containing 2.5 wt. % of crospovidones has proved to be particularly advantageous. Crospovidones are substances preventing agglomeration and sedimentation of the pigments. Both the content of povidones as well as of crospovidones depends on the content of the colored pigments used and also on the hue of the tattooing ink. A black color contains therefore lesser contents of povidone and crospovidone than a white color which contains a higher content of pigments.

In an advantageous embodiment the tattooing ink contains a glass material with constituents of silicon dioxide in the range of 10 wt. % to 90 wt. %. As further constituents potassium oxide CaO as an oxide of the alkaline earth metals in the range of 0.1 wt. % to 50 wt. % and sodium oxide $Na_2O$ as an oxide of the alkali metals in the range of 0.1 wt. % to 60 wt. % are present. In addition, a form of phosphorus oxide, in particular $P_2O_5$ in a content of 0.1 wt. % to 40 wt. %, has been admixed to the mixture.

A tattooing ink, in which the glass has a content of 45 wt. % of silicon dioxide, 24.5 wt. % of calcium oxide, 24.5 wt. % of sodium oxide and 6 wt. % of phosphorus oxide is particularly advantageous. Such a bioactive glass is manufactured by the firm SCHOTT GLAS and is manufactured under the trade name "Vitryxx". This represents a special bioactive glass, which is also used for beauty products and skin care preparations. This glass is distributed by the firm ENGELHARD under the trade name "Actysse BG". The bioactive glass with the above composition is characterized, in particular, by the fact that it has quite a good anti-microbial effect. The proposed tattooing ink benefits likewise from these properties.

Preferably, the tattooing ink has a content of bioactive glass in the range of from 3 wt. % to 8 wt. %. The manufacturing costs of a tattooing ink having such a content of glass are in an economically useful range. For particularly high-quality tattooing inks, the use of glass in the range of from 4.5 wt. % to 5.5 wt. % has proved to be ideal. In particular, optimization tests during the manufacture of the tattooing ink have resulted in the content of glass in the composition of the ink amounting to 5 wt. %. With this content of glass the positive properties of the glass in the tattooing ink are most effective. The remaining properties of the dye, in particular the color quality and light fastness are not affected and are preserved. The content of povidone and crospovidone need not be changed for a glass content of five percent.

Preferably, the glass is provided in the form of small glass particles having a size of from 0.1 μm to 100 μm. From a process-technical point of view it has proved effective to add the bioactive glass in finely pulverized form. The size of the glass particles is then distinctly less than 20 μm, preferably about 1.5 μm. In particular, an addition in powder form proves advantageous for the manufacture of tattooing ink. The glass can then be particularly simply stirred into the ink and mixes very easily.

In the following a specific embodiment of the tattooing ink according to the invention is described in more detail, all constituents being indicated in weight percent:

The composition of a red tattooing ink contains water, colored pigment, povidone, crospovidone and bioactive glass in the form of fine particles. The ink contains 55 wt. % of demineralized water. "Pigment Cl 12490" is used as the red dye. The tattooing ink contains 20 wt. % of red colored pigments. "Kollidon 25" in a concentration of 17.5 wt. % is used as povidone. The content of crospovidone is about 2.5 wt. %, in order to prevent an agglomeration. The substance "Kollidon CL-M" is employed as crospovidone. The glass particles are present in a content of 5 wt. %. The bioactive glass contained in the ink is "Actysse BG" of the firm ENGELHARD. This tattooing ink exhibits very good color and light fastness properties. It is anti-inflammatory and promotes wound healing after tattooing. Due to the anti-microbial action of the bioactive glass contained therein, the formation of germs is excluded, so that even an extended storage of an already opened ink bottle is possible without any problems.

The invention claimed is:

1. A tattooing ink composition comprising:
   water;
   at least one colored pigment;
   at least one binding agent; and
   bioactive glass.

2. The tattooing ink composition according to claim 1, wherein said binding agent is a povidone for binding said pigment with said water.

3. The tattooing ink composition according to claim 2, wherein said povidone is polyvinyl-pyrrolidone.

4. The tattooing ink composition according to claim 3, wherein said water is 35 wt. % to 65 wt. %, said colored pigment is 1 wt. % to 40 wt. %, said povidone is 5 wt. % to 20 wt. %, said bioactive glass is 0.1 wt. % to 10 wt. %, and further comprising 0.1 wt. % to 2.5 wt. % crospovidone.

5. The tattooing ink composition according to claim 4, wherein said bioactive glass is composed of 10 wt. % to 90 wt. % $SiO_2$, 0.1 wt. % to 50 wt. % CaO, 0.1 wt. % to 60 wt. % $Na_2O$, and 0.1 wt. % to 40 wt. % $P_2O_5$.

6. The tattooing ink composition according to claim 5, wherein said bioactive glass is composed of 45 wt. % $SiO_2$, 24.5 wt. % CaO, 24.5 wt. % $Na_2O$, and 6 wt. % $P_2O_5$.

7. The tattooing ink composition according to claim 6, wherein the content of said bioactive glass is in the range of from 3 wt. % to 8 wt. %.

8. The tattooing ink composition according to claim 7, wherein the content of said bioactive glass is in the range of from 4.5 wt. % to 5.5 wt. %.

9. The tattooing ink composition according to claim 8, wherein said bioactive glass is present in the form of small glass particles.

10. The tattooing ink composition according to claim 9, wherein said bioactive glass particles have a size of from 0.1 to 100 micrometers.

11. The tattooing ink composition according to claim 10, wherein said bioactive glass particles are smaller than 20 micrometers.

12. A tattooing ink composition comprising:
    35 wt. % to 65 wt. % of water;
    1 wt. % to 40 wt. % of at least one colored pigment;
    5 wt. % to 20 wt. % of povidone;
    0.1 wt. % to 2.5 wt. % of crospovidone; and
    0.1 wt. % to 10 wt. % of bioactive glass;
    wherein said bioactive glass is composed of 10 wt. % to 90 wt. % $SiO_2$, 0.1 wt. % to 50 wt. % CaO, 0.1 wt. % to 60 wt. % $Na_2O$, and 0.1 wt. % to 40 wt. % $P_2O_5$.

13. The tattooing ink composition according to claim 12, wherein said povidone is polyvinyl-pyrrolidone.

14. The tattooing ink composition according to claim 13, wherein said bioactive glass is composed of 45 wt. % $SiO_2$, 24.5 wt. % CaO, 24.5 wt. % $Na_2O$, and 6 wt. % $P_2O_5$.

15. The tattooing ink composition according to claim 14, wherein the content of said bioactive glass is in the range of from 3 wt. % to 8 wt. %.

16. The tattooing ink composition according to claim 15, wherein the content of said bioactive glass is in the range of from 4.5 wt. % to 5.5 wt. %.

17. The tattooing ink composition according to claim 16, wherein said bioactive glass is present in the form of small glass particles having a size of from 0.1 to 100 micrometers.

18. The tattooing ink composition according to claim 17, wherein said bioactive glass particles are smaller than 20 micrometers.

19. A method of preventing inflammations and reactions in skin from tattooing, which comprises the step of providing a tattooing ink comprising:
(a) 35 wt. % to 65 wt. % of water;
(b) 1 wt. % to 40 wt. % of at least one colored pigment;
(c) 5 wt. % to 20 wt. % of povidone;
(d) 0.1 wt. % to 2.5 wt. % of crospovidone; and
(e) 0.1 wt. % to 10 wt. % of bioactive glass.

20. The method according to claim 19, wherein said bioactive glass is composed of 10 wt. % to 90 wt. % $SiO_2$, 0.1 wt. % to 50 wt. % CaO, 0.1 wt. % to 60 wt. % $Na_2O$, and 0.1 wt. % to 40 wt. % $P_2O_5$.

* * * * *